United States Patent [19]
Beckett et al.

[11] Patent Number: 5,540,496
[45] Date of Patent: Jul. 30, 1996

[54] SOLUTE DISSOLUTION RECIPROCATING FLOW-CELL

[76] Inventors: Arnold H. Beckett, 20 Braybrooke Gardens, Fox Hill, Upper Norwood, London, England; James F. Swon, 12 Twin Park Dr., Brookside, N.J. 07926; Henry Z. Hofer, 30 Bruce Dr., East Hanover, N.J. 07936

[21] Appl. No.: 528,788

[22] Filed: Sep. 18, 1995

[51] Int. Cl.⁶ .................... B01F 15/06; B01F 9/00
[52] U.S. Cl. ................ 366/144; 366/235; 366/239
[58] Field of Search ............................ 366/219, 235, 366/239, 208, 210, 211, 131, 136, 137, 159.1, 160.1, 144, 145, 147, 148, 146, 237, 348, 349

[56] References Cited

U.S. PATENT DOCUMENTS

| | | |
|---|---|---|
| 2,717,700 | 9/1955 | Gruzensky ........................ 366/208 |
| 3,163,404 | 12/1964 | Kraft. |
| 3,501,131 | 3/1970 | Grantham. |
| 3,625,485 | 12/1971 | Apler. |
| 4,893,938 | 1/1990 | Anderson ........................ 366/239 |
| 5,167,928 | 12/1992 | Kelly ........................ 366/208 |
| 5,380,087 | 1/1995 | Haber ........................ 366/130 |

*Primary Examiner*—Robert W. Jenkins
*Attorney, Agent, or Firm*—William T. Hough

[57] ABSTRACT

A combination of a flow-cell with a rate of flow controllable and set to obtain and maintain a solvent or diluent predetermined low flow pressure from the flow-cell's inlet to the flow-cell's outlet, in which at-least an outlet thereof is alternately raised to a height above the inlet thereof sufficiently relative to mass of individual solute(s) and/or individual bead(s) (or other insoluble mass(es)) as to permit the mass of the individual solute(s) and/or individual bead(s) to move by gravity from a direction of the outlet end toward the inlet end of the flow-cell as part of a mechanism ascertainable of improved dissolving of solute and/or suspension of particles of insoluble matter.

74 Claims, 5 Drawing Sheets

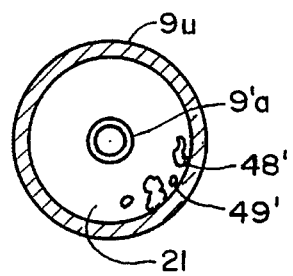
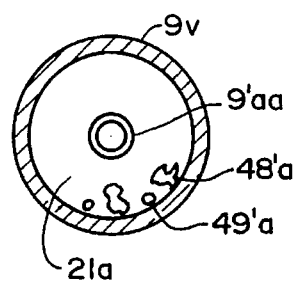
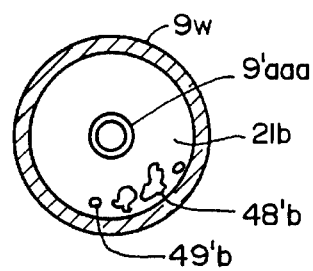
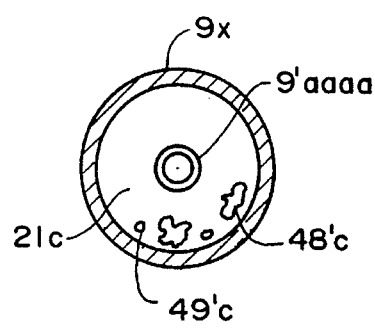
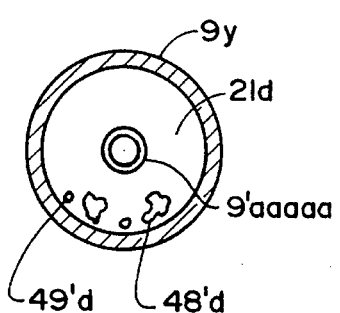
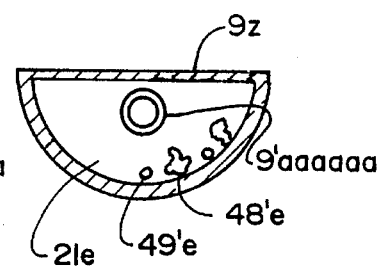
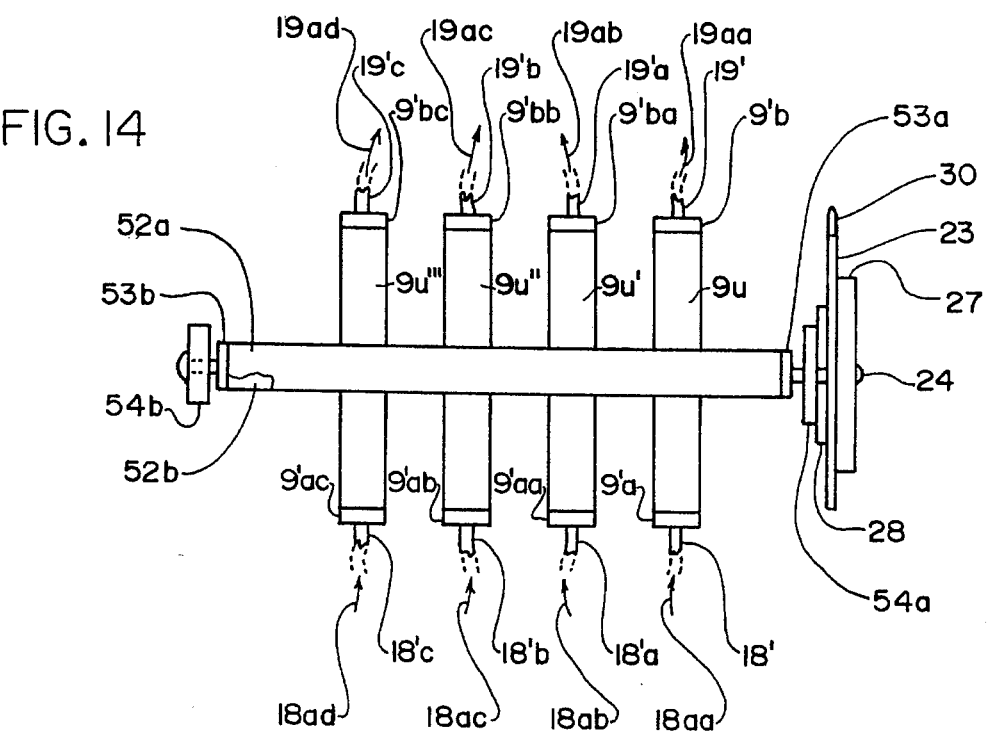

SOLUTE DISSOLUTION RECIPROCATING FLOW-CELL

ACKNOWLEDGED PRIOR ART

A prior art search having been conducted in United States Class 366, subclasses 154.1, 202, 208, 209, 210, 211, 212, 213, 214, 215, 216, 246, while no relevant patents were located, patents and other publication of interest include U.S. Pat. No. 5,380,087 to Haber et al., and U.S. Pat. No. 3,501,131 to Grantham, and U.S. Pat. No. 3,625,485 to Adler, and U.S. Pat. No. 3,163,404 to Kraft et al., and publications Standardized Flow-cell Method as an Alternative to Existing Pharmacopoeial Dissolution Testing, by F. Langenbucher, D. Benz, W. Karuth, H. Moller, and M. Otz—from Ciba-Geigy AG, Hoechst Aktiengesellschaft, Frankfurt/Main (Fed. Rep. of Germany), and Sotax AG, Basel (Switzerland)—portraying the history and various alternative flow through arrangements. That publication discloses various cross-section flow space dimensions relative to rate of flow of the diluent or solvent through the flow space, as associated with various degrees of success in achieving dissolution of solute therein. Also devices for upward flow from a lower inlet to an elevated outlet to the flow space, as shown and discussed. Another flow through known as Dissorest (apparently of LEAP Technologies of Chapel Hill, N.C.) disclosed in a publication therefrom discloses upright orientation such that the solvent or diluent enters from a bottom positioned inlet and flows upwardly toward a top positioned outlet to the flow space for the solvent or diluent circulated therethrough; this publication relates primarily to method(s) of testing the in vitro release of different forms of medicaments.

The Haber patent: This patent is cited as of interest, having no relevance.

The Grantham patent: This patent: discloses a structure for a rocking test tube like vessel for the mixing of closed vessel(s)'s solute static (noncirculating) contents within contained diluent.

The Adler patent: This patent, analogous to that of Grantham, discloses the aforestated static liquid contained within a vessel having solute therein, disclosing for one or more mounted closed test tube like vessels separately but commonly mounted, a mere rotating or rocking mechanism symbolic of shaking the vessel in the hand of a person.

The Kraft patent: This patent, analogous to the aforestated Adler patent, discloses a centrifugal action mounting device, for spinning separately mounted test tube like plugged vessels containing ingredients to be mixed.

BRIEF SUMMARY OF INVENTION

A) Description of the invention having meaning and context in light of existing background, relevant background is as follows, enabling improved understanding of the invention.

Prior to the present invention, consumers have suffered in product quality control as a result of often incomplete dissolving of solute up to a potential maximum solubility, often as a direct result of incomplete and inadequate mixing and/or stirring thereof within the dissolving and/or diluting solvent thereof, and within the available volume thereof. Likewise consumers have suffered from a lack of maximum potential suspensions and from changes in liquid flow properties of colloidal suspensions and the like produced by dissentigration of insoluble products to be tested and/or subsequently utilized. Inadequate mixing and dissolving have resulted heretofore and continue to arise principally as a result of less than maximally effective stirring and/or agitating structures and/or devices, and as a consequence giving flawed and erratic hydrodynamic properties in the vicinity of the products undergoing dissolution of their drug content.

Heretofore there have been basically two alternative approaches to the obtaining of dissolution of solute and/or obtaining suspension of insoluble or minimally soluble aggregate, name as follows. In a liquid or solvent, sometime termed diluent, the sole flowing of the liquid/diluent/solvent into contact with solute or suspendable aggregate has been achieved by either stirring with a blade suspended therein or rotating the solute in a cage or basket, shifting the vessel angularly back and forth such that by gravity the solute or suspendable aggregate shift from one location to another as a result of the alternate tilting of the vessel by way of the angular shifting thereof. The second totally different approach has been to circulate a diluent or solvent from a vessel inlet past and against the solute or aggregate, and outwardly through a vessel outlet; in sole circulating systems the solvent or diluent is solely once circulated through the solute or aggregate containing vessel, while in other alternate systems, the solvent is repeatedly recycled back to the inlet, through the vessel and out of the outlet thereof. In either of the circulating solvent or diluent between the inlet and the outlet, while restraining the undissolved solute or aggregate against exiting from the outlet, there has been included within the space insoluble beads intended to aid the hydrodynamic flow or assist in abrading or crushing the solute or aggregate—but with a major problem of the beads merely being shifted by the flow current of the pumped solvent or diluent, potentially causing the insoluble beads to pile up against a retaining screen and/or to collect with undissolved solute at the screen and/or at the outlet end of the solute containing flow space, potentially impeding and/or retarding diluent flow to and through the outlet and/or otherwise ultimately retarding optimal dissolution of soluble solute. In such situation(s), the insoluble beads disadvantageously tend to pack the solute or aggregate and/or impede the flow of liquid and/or the dissolution of the solute or aggregate as the flowing solvent or diluent moves forcefully toward the outlet of the flow space in which the solute or aggregate and insoluble beads are located.

B) Knowledge and understanding of objects of the invention, make possible improved understanding of the purpose and relevance of the following invention structure(s)/device(s) in light of prior background and present objects, as follow.

One object of the present invention is to obtain a combination device for obtaining improved hydrodynamics around soluble beads of ganulated solute to be tested, to ensure repeatable and consistent dissolution of given amounts of solute or suspendable aggregate in a liquid diluent.

Also an object is to allow use of the diluent in very large volume(s) to allow the dissolution under "sink" conditions of sparingly soluble (low solubility) compound(s) (solute)s) in or of formulated products.

Another object is to make available a combination of laboratory and/or industrial apparatuses by which reliable repeatable concentration of solute aggregate or solute, and/or suspendable aggregate may be consistently maximally obtained through the use of improved mixing devices in both laboratories and in industrial manufacture, obtaining optimal and maximum solution and suspensions reliably ascertainable with regard to stringent government standards.

Another object is to obtain a mixing apparatus or device which by use thereof at low cost of equipment and use thereof makes available to both laboratories and commercial manufacturers the capability of obtaining dissolution under "sink" conditions of drugs of varying solubility and to obtain the most optimum (maximum available) suspensions in all appropriate areas of manufacturing utilization or need thereof irrespective of characteristics of the drug (solute) being dissolved, with reliable consistency in meeting the highest of government standard, beyond realization heretofore.

Another object is to achieve one or more of the foregoing objects, while doing so at minimal costs of equipment and operation thereof.

Another object is to reduce and/or avoid the piling up or caking (compacting against a retainer screen or the like) of undissolved solute at or near a retainer adjacent the outlet end of the enclosed flow space, during an attempted dissolution of solute by attempted mixing thereof with solvent.

Another object is to cause during attempted mixing thereof, solute and/or drug delivery system, to travel against a direction of flow, by travel of undissolved solute from the outlet end toward the inlet end against the direction of flow of solvent traveling through a dissolution flow space.

Another object is to increase the degree of counter directional flow and contact between solvent and undissolved solute or drug delivery system.

Another object is to obtain intermittent alternating movement of insoluble matter in counterflow movement alternately toward a solvent inlet end and toward the outlet end, in and/or transverse to the path and/or position of solute or drug delivery system within a flow path of travel, to crush and/or abrade undissolved solute within solvent in a solvent unidirectional flow path.

Another object is maximize turbulance to which insoluble matter is subjected with or without use of insoluble abrading and/or mixing beads during travel of diluent (solvent) from a diluent inlet to an outlet at an opposite end of a dissolution flow path for mixing solute and/or dispersible matter within solvent and/or diluent, to thereby result in improved and/or maximum dissolving and/or suspension of solute and/or colloidal particles.

Another object is to improve and maximize dissolution and/or obtaining suspension, at optimum temperature of solubility and/or producing suspension of an undissolved solute or suspendable matter at and to maintain dissolution and/or suspension by maintaining optimal temperature (s) of the solution and solute after dissolution and/or suspension, such as the conventionally utilized temperature of 37 degrees Centigrade for dissolution of solute of or dissolving of drug(s) of from pharmaceutical products in their nature.

Other objects become apparent from the preceding and following disclosure.

C) Brief summary of the invention:

Broadly a first broad invention may be defined as a solute dissolution reciprocating flow-cell device as a combination that includes:

A) a solute dissolution flow-cell:

a) having substantially opposite inlet flow structure and outlet flow structure, having inwardly since closing walls forming solute mounting and liquid flow space therein extending substantially between said inlet flow structure and said outlet flow structure, b) said inlet flow structure forming an inlet and said outlet flow structure forming an outlet, said inlet and said outlet each being in flow communication with said liquid flow space, and c) including solute retaining means for introducing into and retaining undissolved solute within the liquid flow space substantially between the inlet and the outlet;

B) elevation structures (and mechanism(s) thereof) for alternately raising and lowering at-least one of a) the inlet flow structure and inlet thereof, and b) the outlet flow structure and outlet thereof, at-least one of above and below the other a predetermined number of angular degrees while substantially concurrently critically obtaining and critically maintaining at a critical predetermined rate of movement and flow of solvent between the inlet and the outlet, for jointly (1) the predetermined number of angular degrees to be of sufficient elevation and 2) the predetermined rate to be sufficiently low as to alternately:

a) critically permit gravity movement of undissolved solute through liquid flowing in critically an opposite direction to critical gravity movement of undissolved solute positioned between the inlet and the outlet within the liquid flow space whenever gravity movement is in a direction toward the inlet and b) intermittently alternately permit undissolved solute to move in the same direction as liquid flowing from the inlet to the outlet thereby to alternately shift undissolved solute in opposite directions along the flow path within the liquid flow space, and C) pump structures (and mechanism(s) thereof) for causing liquid to flow from a liquid source sequentially into the inlet, through the flow liquid space and out of the outlet at the critical predetermined rate and pressure at-least when the outlet is at an elevation higher than elevation of the inlet.

In a first preferred embodiment as an improvement on the first broad invention, the solute dissolution flow-cell and flow path thereof are substantially at-least hemispherical in shape, enabling the solute to slide along typically inner lower concave surfaces along the flow path as the inlet and the outlet of solute dissolution flow-cell are alternately raised and lowered.

In a second preferred embodiment as an improvement on the first preferred embodiment of the first broad invention, the solute dissolution flow-cell and flow path thereof are substantially spherical in shape. This shape, while also achieving the capabilities of the lower hemispherical with its inner concave bottom, concurrently provides increased flow space height substantially medially between the inlet and the outlet, thereby affording a greater moving cross-section of diluent moving toward the outlet during the shifting of the undissolved solute or nonsuspended aggregate being shifted or tumbled toward the inlet as and whenever the outlet end is raised to a level above the inlet end.

In a third preferred embodiment as an improvement on the first preferred embodiment of the first broad invention, the solute dissolution flow-cell and flow path thereof are substantially elliptical in shape, thereby extending the length of the curvature, decreasing the angle thereof, of the concave upwardly facing bottom surface in contact with the solvent and solute advantageously passing or sliding or tumbling thereon and/or thereover with improved mixing and dissolving of the solute, and/or suspension of nonsuspended aggregate.

In a fourth preferred embodiment as an improvement on the third preferred embodiment of the first broad invention of the first broad invention, the solute dissolution flow-cell and flow path thereof are substantially cylindrical and linear between the inlet flow structure and the outlet flow structure, and the solute dissolution flow-cell and flow path thereof are elongated along a longitudinal axis extending substantially between the inlet and the outlet as compared to transverse directions. The tumbling, sliding, rolling or the like, of undissolved and/or nonsuspended solute and/or aggregate, is enhanced by the extended cylindrical length of the solute dissolution flow-cell, but still retaining the advantages of the concave bottom along the transverse axis to the longitudinal axis of the cylindrically shaped solute dissolution flow-cell.

In a fifth preferred embodiment as an improvement on the fourth preferred embodiment of the first broad invention, the solute dissolution flow-cell has a flow path cross-section extending substantially from the inlet to the outlet, and includes within the flow space at least one substantially insoluble member having an insoluble member cross-section sufficiently smaller than at-least a part of the flow path cross-section and having a mass sufficiently massive as to be moveable by gravity toward the inlet against flow of the solvent at the predetermined pressure when the outlet is at an elevation higher than the inlet. While there maybe a plurality thereof of the same or diverse sizes, each or alternately mere a part of (lesser than 100 percent thereof) may be of small dimension(s) substantially less than the cross-sectional flow of the flow path, or alternatively may be of more than 50% of the flow path—depending upon the nature of the solute, so as to adapt size to total weight and slideability responsive to gravitational pull thereon as one or the other of the inlet and the outlet is raised or lowered, to shift the mixing and/or crushing and/or abrading toward and/or over/against undissolved solute each when shifting toward the inlet (when the inlet is below the level of the outlet) and when shifting toward the outlet (when the inlet is above the level of the outlet).

In a sixth preferred embodiment as an improvement on the fifth preferred embodiment of the first broad invention, the substantially insoluble member is present in plurality and the plurality is substantially bead like in shape. Based on pure physics, smaller insoluble disks, chips, beads or the like, for a same predetermined total weight, have a greater surface area, whereby more numerous small insoluble members are typically more effective in achieving mixing and/or crushing of the solute (assisting in the dissolving thereof)—provided the mass thereof is/are sufficiently large as to facilitate being shiftable by gravity against the force of flow of liquid/diluent/solvent toward the outlet from the inlet, whereby, a plurality of smaller members is more effective and preferred.

In a seventh preferred embodiment as an improvement on the sixth preferred embodiment of the first broad invention, there is further included heater-circulator structures (and mechanism(s) thereof) for ascertaining that solvent at a time of entry of solvent through the inlet is substantially maintained substantially at an optimal predetermined desired temperature that is consistent with the ultimate end-use such as for thereafter the testing of the amount of solute as to be determined by a subsequent testing-evaluation, when dissolving within a predetermined solvent to be circulated into contact with a predetermined solute. An example of such situation would be for dissolving under conditions and in amounts less that total saturation of the dissolving liquid, as in the case where subsequent testing will be dissolution testing of pharmaceutical products—a main area of use and purpose of the present invention. While aforestated features enhance dissolution and obtaining of solution and/or suspension of solute and/or aggregate, as to "soluble" solute (to one degree or another), solute normally is optimally soluble at one particular temperature or range of temperatures, differing for different solutes. Accordingly, adjusted to test temperature and to adjust temperature to the optimal dissolution temperature for a particular solute, further enhances/improves overall dissolution of undissolved solute. Thereby, the inclusion of the heater-circulator as a part of this particular inventive combination, further improve the rate of achieving dissolution together with a further improved greater extent of dissolution.

In a eighth preferred embodiment as an improvement on the seventh preferred embodiment of the first broad invention, there is included at-least one heater-circulator ascertainable of and maintainable of substantially optimum solubility temperature of solute containing solvent that has flowed through the outlet, for the same scientific bases as aforestated for the sixth preferred embodiment.

In a ninth preferred embodiment as an improvement on the eighth preferred embodiment of the first broad invention, there is included closed flow structures (and mechanism(s) thereof) for diverting at-least a portion of solute containing solvent passing from the outlet, in at-least partially closed flow back to the inlet. While as acknowledged in prior art aforestated there exists an option of closed flow cycle, as opposed to one time through; because of improved ability to achieve maximum dissolution by the present invention, a closed or partially closed cycle (recycling) of solvent/diluent for the present invention has the additional advantage of obtaining higher concentration(s) of the dissolved solute(s) devoid of any likely potential problem of decreasing probability of further dissolution because of already existing high solute concentration in the recirculated solution. Accordingly, both greater dissolution and also higher potential concentration(s) thereof are possible by the present invention, by utilizing recycling of the solvent and solution.

In a tenth preferred embodiment as an improvement on the ninth preferred embodiment of the first broad invention, there is included in parallel on the elevation structures (and mechanism(s) thereof) a plurality of the solute dissolution flow-cell mounted for concurrently the elevation structures (and mechanism(s) thereof) alternately raising thereof at-least one of a) the inlet flow structure and inlet thereof, and b) the outlet flow structure and outlet thereof, of the plurality, such that concurrently at least one of the inlet and the outlet of each of the plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents, particularly as here where the present invention and preferred embodiments thereof serve to achieve a greater degree of dissolution and thus a possible greater eventual concentration.

In an eleventh preferred embodiment as an improvement on the tenth preferred embodiment of the first broad invention, substantially average cross-sectional diameter of the flow space ranges between about 10 mm to about 25 mm and the predetermined rate of flow per minute ranges from about 3 milliliters to about 20 milliliters per minute. These parameters are susceptable to minor or greater variations depending upon the nature of the particular solute, the particular solvent, and the rate of flow of the solvent through the flow path, as well as the temperature of the solvent passed through the flow path. Accordingly, this parameter is based on prior experimental results by aforestated publications above discussed, as it relates to the present invention as one or more preferred embodiments thereof.

In a twelfth preferred embodiment as an improvement on the eleventh preferred embodiment of the first broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 10 angular degrees and about 180 angular degrees. The same controlling factors relate as set-forth in the preceding paragraph for the eleventh preferred embodiment.

In a thirteenth preferred embodiment as an improvement on the eleventh preferred embodiment of the first broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 45 angular degrees and about 90 angular degrees. The same controlling factors relate as set-forth in the preceding paragraph for the eleventh preferred embodiment.

In a fourteenth preferred embodiment as an improvement on the thirteenth preferred embodiment of the first broad invention, the elevation structures (and mechanism(s) thereof) are adapted to pivot concurrently the inlet flow structure downwardly and the outlet flow structure upwardly around a pivot point substantially centrally intermediate between the inlet and the outlet. By this arrangement, together with aforestated critical limitations as to predetermined rate of flow and size and weight (mass) of the solute, the intermediate positioning of a pivot point reduces the length of arc(s) of travel of either or both the inlet and the outlet as one or both thereof are alternately shifted upwardly and downward as aforestated, thereby being more compact.

In a fifteenth preferred embodiment as an improvement on the first preferred embodiment of the first broad invention, the solute dissolution flow-cell and flow path thereof are substantially spherical in shape. The advantages thereof have been previously above discussed already.

In a sixteenth preferred embodiment as an improvement on the first broad invention, the solute dissolution flow-cell has a flow path cross-section extending substantially from the inlet to the outlet, and includes within the flow space at least one substantially insoluble member having an insoluble member cross-section sufficiently smaller than at-least a part of the flow path cross-section and having a mass sufficiently massive as to be moveable by gravity toward the inlet against flow of the solvent at the predetermined pressure when the outlet is at an elevation higher than the inlet. The greater the length of the flow path, the more improved/ enhanced is the opportunity for optimal dissolution of solute within the flow path, as well as a longer flow path being receivable of a greater amount of solute therein to be dissolved by flow of solvent/diluent from the inlet to and out of the outlet.

In a seventeenth preferred embodiment as an improvement on the sixteenth preferred embodiment of the first broad invention, the substantially insoluble member is present in plurality and the plurality thereof substantially each thereof being substantially bead like in shape, for aforestated reasons and advantages thereof.

In an eighteenth preferred embodiment as an improvement on the first broad invention, there is included heater-circulator structures (and mechanism(s) thereof) for ascertaining that solvent at a time of entry of solvent through the inlet is substantially maintained substantially at predetermined optimal temperature of diluent/solution at which a predetermined solute placed within the flow path is at a predetermined solubility within a predetermined solvent to be circulated into contact with a predetermined solute, for aforestated reasons and advantages thereof.

In a nineteenth preferred embodiment as an improvement on the first broad invention, there is included at-least one heater-circulator ascertainable of and maintainable of predetermined optimum solubility temperature of solvent designated for to be dissolved, where the solvent retaining and/or conduit structure results in the diligent being flowed consecutively through the inlet and eventually outwardly through the outlet, for aforestated reasons and advantages thereof.

In a twentieth preferred embodiment as an improvement on the first broad invention, there are included closed flow structures (and mechanism(s) thereof) for diverting at-least a portion of solute containing solvent passing from the outlet, in at-least partially closed flow back to the inlet, for aforestated cyclic flow reasons and advantages thereof.

In a twenty-second preferred eminent as an improvement on the first broad invention, there are included in parallel on the elevation structures (and mechanism(s) thereof) a plurality of separate ones of the solute dissolution flow-cell mounted for concurrently elevation structures (and mechanism(s) thereof) alternately raising thereof at-least one of a) the inlet flow structure and inlet thereof, and b) the outlet flow structure and outlet thereof, of the plurality, such that concurrently at least one of the inlet and the outlet of each of the plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents. Improved capacity of concurrently mixing of separate self-contained different solutes and solvents and the like, are made possible by the simplicity of structure and arrangements of the structures of the present invention, for improved utility and potential increased production using the device for concurrent mixing of several different solute dissolution flow-cells.

In a twenty-second preferred embodiment as an improvement on the first broad invention, substantially average cross-sectional diameter of the flow space ranges between about 10 mm to about 25 mm and the predetermined rate of flow per minute ranges from about 3 milliliters to about 20 milliliters per minute for reasons and advantages aforestated.

In a twenty-third preferred embodiment as an improvement on the first broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 10 angular degrees and about 180 angular degrees for reasons and advantages aforestated.

In a twenty-fourth preferred embodiment as an improvement on the first broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 45 angular degrees and about 90 angular degrees for reasons and advantages aforestated.

In a twenty-fifth preferred embodiment as an improvement on the first broad invention, the elevation structures (and mechanism (s) thereof) are adapted to pivot concurrently the inlet flow structure downwardly and the outlet flow structure upwardly around a pivot point substantially centrally intermediate between the inlet and the outlet for reasons and advantages aforestated.

In a second broad embodiment of the invention second solute dissolution reciprocating flow-cell as alternate combination includes:

A) a solute dissolution flow-cell:

a) having substantially opposite inlet flow structure and outlet flow structure, having inwardly space closing walls forming solute mounting and liquid flow space therein extending substantially between the inlet flow structure and the outlet flow structure, b) the inlet flow structure forming an inlet and the outlet flow structure forming an outlet, the inlet and the outlet each being in flow communication with the liquid flow space, c) including solute retaining structures (and mechanism(s) thereof) for introducing into and retaining undissolved solute within the liquid flow space substantially between the inlet and the outlet;

d) the solute dissolution flow-cell having a flow path cross-section extending substantially from the inlet to the outlet; and e) there being within the flow space at least one substantially insoluble member having an insoluble member cross-section sufficiently smaller than at-least a part of the flow path cross-section as to be moveable along the flow path; and B) elevation structures (and mechanism(s) thereof) for alternately raising and lowering at-least one of a) the inlet flow structure and inlet thereof, and b) the outlet flow structure and outlet thereof, at-least one of above and below the other a predetermined number of angular degrees while substantially concurrently obtaining and maintaining at a predetermined rate of movement and flow of solvent between the inlet and the outlet, for jointly (1) the predetermined number of angular degrees to be of sufficient elevation and 2) the predetermined rate to be sufficiently low as to alternately:

a) permit gravity movement of the at least one substantially insoluble member through liquid flowing in an opposite direction to gravity movement of the at least one substantially ,insoluble member positioned between the inlet and the outlet within the liquid flow space whenever gravity movement is in a direction toward the inlet and b) intermittently alternately permit the at least one insoluble member to move in the same direction as liquid flowing from the inlet to the outlet thereby to alternately shift the at least one insoluble member to move alternately in opposite directions along the flow path within the liquid flow space, and C) pump structures (and mechanism(s) thereof) for causing liquid to flow from a liquid source sequentially into the inlet, through the flow liquid space and out of the outlet at the critical predetermined rate and critical pressure at-least when the outlet is critically at an elevation higher than elevation of the inlet. The underlying reasons and advantages are the same as for the first broad invention.

Additionally, however, this alternate second broad invention critically requires the presence of the aforestated insoluble member(s) of the sufficient mass (weight) as to move back and forth along the flow path responsive to the alternating shifting upwardly and downwardly of at-least one or both of the inlet and the outlet, per aforestated discussion and disclosure, but especially noting that the presence of this shifting element obviate the criticality of the solute being of sufficient mass (weight) for the undissolved solute to shift, since the shifting insoluble member serves to strike, abrade, crush and/or otherwise enhance and/or facilitate the rate and degree of potentially maximum dissolving of the solute within the flow path as solvent/diluent passes from the inlet to and out of the outlet.

As a first preferred embodiment on the alternate second broad invention, the solute dissolution flow-cell and flow path thereof are substantially at-least hemispherical in shape, for aforestated reasons and advantages.

As a second preferred embodiment on the alternate second broad invention, the solute dissolution flow-cell and flow path thereof are substantially spherical in shape, for aforestated reasons and advantages.

As a third preferred embodiment on the alternate second broad invention, the solute dissolution flow-cell and flow path thereof are substantially elliptical in shape for aforestated reasons and advantages.

As a fourth preferred embodiment on the alternate second broad invention, the solute dissolution flow-cell and flow path thereof are substantially cylindrical and linear between the inlet flow structure and the outlet flow structure, and the solute dissolution flow-cell and flow path thereof are elongated along a longitudinal axis extending substantially between the inlet and the outlet as compared to transverse directions for aforestated reasons and advantages.

As a fifth preferred embodiment on the alternate second broad invention, the substantially insoluble member is present in plurality and the plurality being substantially bead like in shape for aforestated reasons and advantages.

As a sixth preferred embodiment on the fifth preferred embodiment of the alternate second broad invention, there is included heater-circulator structures (and mechanism(s) thereof) for ascertaining that solvent at a time of entry of solvent through the inlet is substantially maintained substantially at an optimal temperature at which a predetermined solute placed within the flow path is at substantially maximum solubility within a predetermined solvent to be circulated into contact with a predetermined solute for aforestated reasons and advantages.

As a seventh preferred embodiment on the fourth preferred embodiment on the alternate second broad invention, there is included at-least one heater-circulator ascertainable of and maintainable of substantially optimum solubility temperature of solute containing solvent that has flowed through the outlet for aforestated reasons and advantages.

As a eighth preferred embodiment on the sixth preferred embodiment of the alternate second broad invention, there are included closed flow structures (and mechanism(s) thereof) for diverting at-least a portion of solute containing solvent passing from the outlet, in at-least partially closed flow back to the inlet for aforestated reasons and advantages.

As a ninth preferred embodiment on the eighth preferred embodiment of the alternate second broad invention, there are included in parallel on the elevation structures (and mechanism(s) thereof) a plurality of the solute dissolution flow-cell mounted for concurrently the elevation structures (and mechanism(s) thereof) alternately raising thereof at-least one of a) the inlet flow structure and inlet thereof, and b) the outlet flow structure and outlet thereof, of the plurality, such that concurrently at least one of the inlet and the outlet of each of the plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents for aforestated reasons and advantages.

As a tenth preferred embodiment on the ninth preferred embodiment of the alternate second broad invention, substantially average cross-sectional diameter of the flow space ranges between about 10 mm to about 25 mm and the predetermined rate of flow per minute ranges from about 3 milliliters to about 20 milliliters per minute for aforestated reasons and advantages.

As an eleventh preferred embodiment on the tenth preferred embodiment of the alternate second broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 10 angular degrees and about 180 angular degrees for aforestated reasons and advantages.

As a twelfth preferred embodiment on the tenth preferred embodiment of the alternate second broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 45 angular degrees and about 90 angular degrees for aforestated reasons and advantages.

As a thirteenth preferred embodiment on the twelfth preferred embodiment of the alternate second broad invention, the elevation structures (and mechanism(s) thereof) are adapted to pivot concurrently the inlet flow structure downwardly and the outlet flow structure upwardly around a pivot point substantially centrally intermediate between the inlet and the outlet for aforestated reasons and advantages.

As a fourteenth preferred embodiment on the first preferred embodiment of the alternate second broad invention, the solute dissolution flow-cell and flow path thereof are substantially spherical in shape for aforestated reasons and advantages.

As a fifteenth preferred embodiment on the alternate second broad invention, second broad invention, the solute dissolution flow-cell has a flow path cross-section extending substantially from the inlet to the outlet, and additionally there is included within the flow space at least one substantially insoluble member having an insoluble member cross-section sufficiently smaller than at-least a part of the flow path cross-section and having a mass sufficiently massive as to be moveable by gravity toward the inlet against flow of the solvent at the predetermined pressure when the outlet is at an elevation higher than the inlet for aforestated reasons and advantages.

As a sixteenth preferred embodiment on the alternate second broad invention, the substantially insoluble member is present in plurality and the plurality being substantially bead like in shape for aforestated reasons and advantages.

As a seventeenth preferred embodiment on the alternate second broad invention, there are included heater-circulator structures (and mechanism(s) thereof) for ascertaining that solvent at a time of entry of solvent through the inlet is substantially maintained substantially at an optimal temperature at which a predetermined solute placed within the flow path is at substantially maximum solubility within a predetermined solvent to be circulated into contact with a predetermined solute for aforestated reasons and advantages.

As a eighteenth preferred embodiment of the alternate second broad invention, there is included at-least one heater-circulator ascertainable of and maintainable of substantiality optimum solubility temperature of solute containing solvent that has flowed through the outlet for aforestated reasons and advantages.

As a nineteenth preferred embodiment of the alternate second broad invention, there are included closed flow structures (and mechanism(s) thereof) for diverting at-least a portion of solute containing solvent passing from the outlet, in at-least partially closed flow back to the inlet for aforestated reasons and advantages.

As a twentieth preferred embodiment of the alternate second broad invention, there are including in parallel on the elevation structures (and mechanism(s) thereof) a plurality of the solute dissolution flow-cell mounted for concurrently the elevation structures (and mechanism (s) thereof) alternately raising thereof at-Least one of a) the inlet flow structure and inlet thereof, and b) the outlet flow structure and outlet thereof, of the plurality, such that concurrently at least one of the inlet and the outlet of each of the plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents for aforestated reasons and advantages.

As a twenty-first preferred embodiment of the alternate second broad invention, substantially average cross-sectional diameter of the flow space ranges between about 10 mm to about 25 mm and in which the predetermined rate of flow per minute ranges from about 3 milliliters to about 20 milliliters per minute for aforestated reasons and advantages.

As a twenty-second preferred embodiment of the alternate second broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 10 angular degrees and about 180 angular degrees for aforestated reasons and advantages.

As a twenty-third preferred embodiment of the alternate second broad invention, the elevation structures (and mechanism(s) thereof) are adapted to move at-least one of the inlet flow structure and the outlet flow structure relative to at-least one of a) a pivot point therebetween and b) a remaining other of the inlet flow structure and the outlet flow structure, through an angle of the predetermined angular degrees ranging from about 45 angular degrees and about 90 angular degrees for aforestated reasons and advantages.

As a twenty-fourth preferred embodiment of the alternate second broad invention, the elevation structures (and mechanism(s) thereof) are adapted to pivot concurrently the inlet flow structure downwardly and the outlet flow structure upwardly around a pivot point substantially centrally intermediate between the inlet and the outlet for aforestated reasons and advantages.

As a twenty-fifth preferred embodiment on the alternate second broad invention, with either of one of the inlet end and the outlet angled relative to the remaining one thereof at a predetermined number of angular degrees while substantially concurrently obtaining and maintaining at predetermined rate of movement and flow of solvent between the inlet and the outlet, for jointly (1) the predetermined number of angular degrees is to be of sufficient elevation and 2) the predetermined rate to be sufficiently low as to alternately:

a) permit gravity movement of undissolved solute through liquid flowing in an opposite direction to gravity movement of undissolved solute positioned between the inlet and the outlet within the liquid flow space whenever gravity movement is in a direction toward the inlet and b) intermittently alternately permit undissolved solute to move in the same direction as liquid flowing from the inlet to the outlet thereby to alternately shift undissolved solute in opposite directions along the flow path within the liquid flow space for aforestated reasons and advantages.

As a twenty-sixth preferred embodiment on the sixteenth preferred embodiment of the alternate second broad invention, the predetermined rate of movement and flow of solvent between the inlet and the outlet is sufficiently low as to alternately:

a) permit gravity movement of undissolved solute through liquid flowing in an opposite direction to gravity movement of undissolved solute positioned between the inlet and the outlet within the liquid flow space whenever gravity movement is in a direction toward the inlet and b) intermittently alternately permit undissolved solute to move in the same direction as liquid flowing from the inlet to the outlet thereby to alternately shift undissolved solute in opposite directions along the flow path within the liquid flow space for aforestated reasons and advantages.

As a twenty-seventh preferred embodiment on twenty-sixth preferred embodiment of the alternate second broad invention, the undissolved solute is in a liquid state for aforestated reasons and advantages.

As a twenty-eighth first preferred embodiment on the alternate second broad invention, the undissolved solute is in a liquid state for aforestated reasons and advantages.

As a twenty-sixth preferred embodiment on the fourteenth preferred embodiment on the first broad invention, the undissolved solute is in a liquid state for aforestated reasons and advantages.

As a twenty-seventh preferred embodiment on the first broad invention, the undissolved solute is in a liquid state for aforestated reasons and advantages.

As a twenty-ninth preferred embodiment on the alternate second broad invention, the predetermined rate of movement and flow of solvent between the inlet and the outlet is sufficiently low as to alternately:

a) permit gravity movement of undissolved solute through liquid flowing in an opposite direction to .gravity movement of undissolved solute positioned between the inlet and the outlet within the liquid flow space whenever gravity movement is in a direction toward the inlet and b) intermittently alternately permit undissolved solute to move in the same direction as liquid flowing from the inlet to the outlet thereby to alternately shift undissolved solute in opposite directions along the flow path within the liquid flow space for aforestated reasons and advantages.

As a twenty-eighth preferred embodiment on the first broad invention, there is included undissolved solute within the liquid flow space substantially between the inlet and the outlet for aforestated reasons and advantages.

As a twenty-ninth preferred embodiment on the fourteenth preferred embodiment of the first broad .invention, there is included undissolved solute within the liquid flow space substantially between the inlet and the outlet for aforestated reasons and advantages.

As a thirtieth preferred embodiment on the alternate second broad invention, there is included undissolved solute within the liquid flow space substantially between the inlet and the outlet for aforestated reasons and advantages.

As a thirty-first preferred embodiment on the thirteenth preferred embodiment of the alternate second broad invention, there is included undissolved solute within the liquid flow space substantially between the inlet and the outlet for aforestated reasons and advantages.

As a thirtieth preferred embodiment on the first broad invention, there is included the solvent within the liquid flow space substantially between the inlet and the outlet for aforestated reasons and advantages.

As a thirty-first preferred embodiment on twenty-ninth preferred embodiment of the first broad invention, there is included the solvent within the liquid flow space substantially between the inlet and the outlet for aforestated reasons and advantages.

As a thirty-second preferred embodiment of the thirtieth preferred embodiment on the alternative second broad invention, there is included the solvent within the liquid flow space substantially between the inlet and the outlet for aforestated reasons and advantages.

As a thirty-first preferred embodiment on the thirty-first preferred embodiment of the alternate second broad invention, there is included the solvent the liquid flow space substantially between the inlet and the outlet for aforestated reasons and advantages.

As a thirty-second preferred embodiment on the first broad invention, there is included the solvent within the liquid flow space substantially between the inlet and the outlet for aforestated reasons and advantages.

As a thirty-third preferred embodiment on fourteenth preferred embodiment of the first broad invention, there is included the solvent within the liquid flow space substantially between the inlet and the outlet for aforestated reasons and advantages.

As a thirty-second preferred embodiment on the alternate second broad invention, there is included the solvent within the liquid flow space substantially between the inlet and the outlet for aforestated reasons and advantages.

As a thirty-third preferred embodiment on the thirteenth preferred embodiment of the alternate second broad invention, there is included the solvent within the liquid flow space substantially between the inlet and the outlet for aforestated reasons and advantages.

As a thirty-fourth preferred embodiment on thirty-second preferred embodiment of the first broad invention, the solvent is predominantly water for aforestated reasons and advantages.

As a thirty-fifth preferred embodiment on thirty-third preferred embodiment of the first broad invention, the solvent is predominantly water for aforestated reasons and advantages.

As a thirty-fourth preferred embodiment on the thirty-second preferred embodiment of the alternate second broad invention, the solvent is predominantly water for aforestated reasons and advantages.

As a thirty-fifth preferred embodiment on the thirty-third preferred embodiment of the alternate second broad invention, thirty-third solute dissolution reciprocating flow-cell device of the thirty-third preferred embodiment of the second broad invention, solvent is predominantly water for aforestated reasons and advantages.

In another embodiment generic to each of the first and second broad invention, the elevation structures (and mechanism thereof) in the predetermined rate of flow within the scope thereof, a) permits gravity movement of at-least one of [1] undissolved solute and [2] at least one substantially insoluble member, through liquid flowing in an opposite direction to gravity movement of undissolved solute positioned between said inlet and said outlet within said liquid flow space whenever gravity movement is in a direction toward said inlet and b) intermittently alternately permit at least one of [1] undissolved solute and [2] at least one insoluble member, to move in the same direction as liquid flowing from the inlet to the outlet thereby to alternately shift undissolved solute in opposite directions along said flow path within said liquid flow source.

BRIEF DESCRIPTION OF THE DRAWINGS

FIGS. 8, 9, 10 11, 12 and 13 respectively illustrate cross-sectional views as taken along line 8—8 of FIG. 2, line 9—9 if FIG. 3, 10—10 of FIG. 4, line 11—11 of FIG. 5, line 12—12 of FIG. 6, and line 13—13 of FIG. 7 respectively in symbolic diagrammatic representations thereof.

FIG. 14 is a symbolic and diagrammatic top view representation of the aforenoted invention as illustrated in FIG. 2, taken along lines 14—14 of FIG. 2, as embodied with a structure and mechanism for concurrently alternately raising and lowering the inlet end of a plurality of flow-cells relative to their outlet ends, such that a single drive and combination represented by FIG. 1, serves to function on a plurality of separate flow-cells concurrent for the same and/or different solute(s) and/or suspendable aggregate(s) and/or solvent(s) and/or diluent(s).

DETAILED DESCRIPTION

The device of the present invention serves to improve counter flow contact of solute with solvent and/or diluent moving always constantly from the flow through vessel toward and out of the outlet thereof, together with a continuing and repeated shifting of the solute or aggregate and/or beads within the flow space alternately toward the inlet and intermittently oppositely toward the outlet. As a result thereof, the solute dissolution has been enhanced, and likewise for a suspendable aggregate, maximum suspension is achievable. Even further enhancement in the speed and effectiveness of maximal dissolving and/or suspending the solute and/or aggregate is achieved by utilization in the flow path sequence of flow a temperature detecting and adjustment heater-circulator —as aforestated in the preceding description of various embodiments. As also aforestated, the rate of flow through the flow space is critical and must be adapted to the mass (weight) and/or bulk of the solute and/or aggregate. Likewise, for light weight solute or other aggregate, the utilization of insoluble beads or other insoluble shifting abrading and/or crushing elements serve to shift against and/or abrade and/or crush residual undissolved and/or unsuspended solute and/or aggregate.

Figure 1:
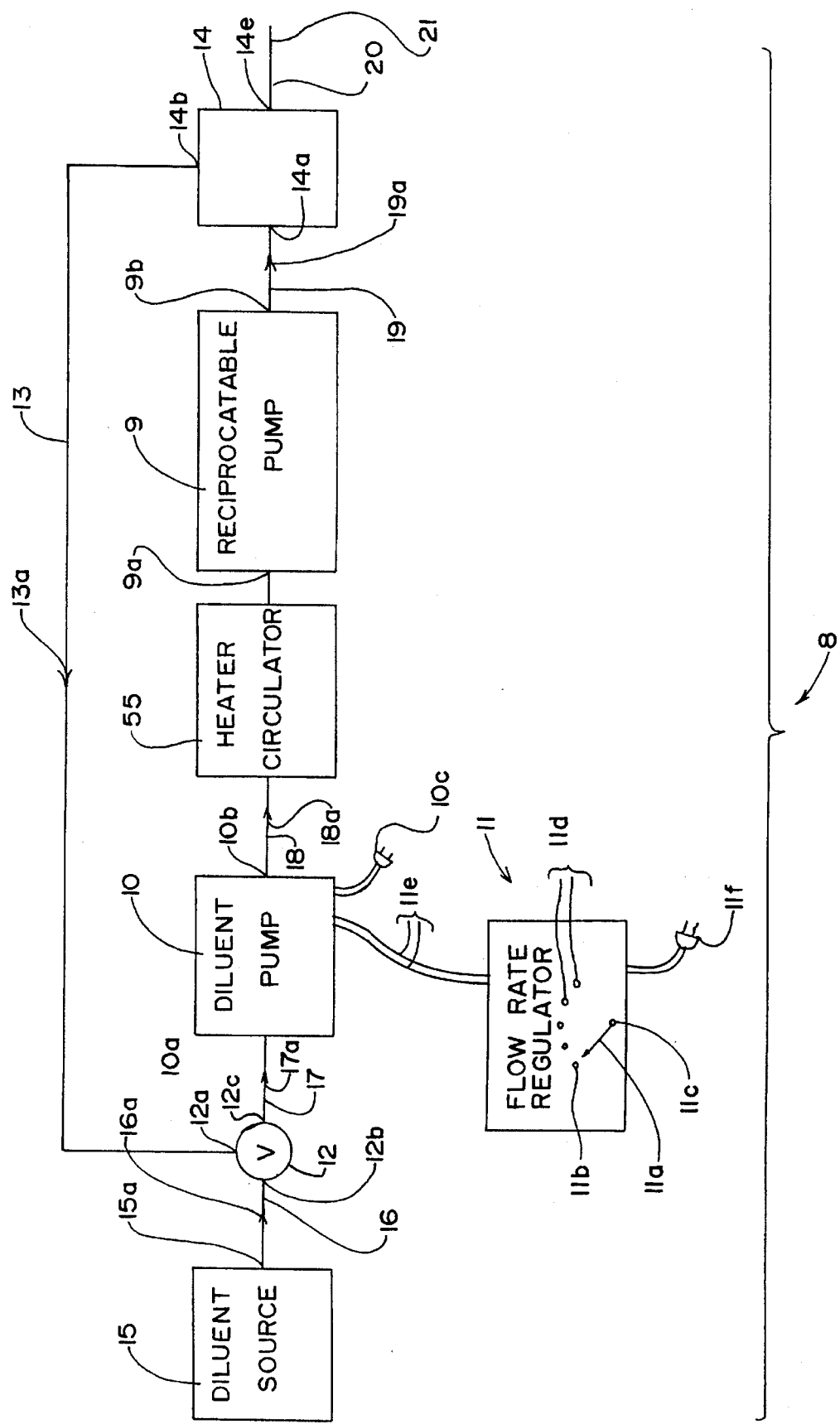
FIG. 1 diagrammatically and symbolically illustrates an entire combination embodying in a flow diagram the generic invention and preferred embodiments thereof, of the reciprocatable flow-cell, diluent pump, flow rate regulator of diluent pump, alternate diluent-source flow valve, solution collection vessel, recyle flow connection to the alternate diluent-source flow valve, diluent source, and flow connections between the diluent source, the diluent pump, the reciprocatable flow-cell, and the solution collection vessel.

With reference to FIG. 1, FIG. 1 diagrammatically and symbolically illustrates an entire combination 8, in the form of a flow diagram, as to the generic invention and preferred embodiments thereof. There is shown the reciprocatable flow-cell 9, a diluent pump 10, flow rate regulator 11 of diluent pump 10, an alternate diluent-source flow valve 12, a solution collection vessel 13, a recyle flow connection (i.e., conduit) 13 for flow in direction 13a from the solution collection vessel 14 to the alternate diluent-source flow valve 12, a diluent source 15, and flow connections (conduits). Typically illustrated are operative conduits and valves, etc. thereof—such as conduit 16 between the diluent source 15 from its diluent source outlet 15a and the valve inlet 12b of alternate flow variable valve 12 for flow in direction 16a, and conduit 17 between the valve outlet 12c and the diluent pump's inlet 10a for flow in direction 17a, the conduit 18 from the pump 10 through heat-circulator 53 to the reciprocatable flow-cell 9 in direction 18a, the conduit 19 between the reciprocatable flow-cell 9 and the solution collection vessel 13 for flow in direction 19a to the solution collection vessel 14. Also there is the conduit 20 from the solution collection vessel withdrawal outlet 14c, through which collected solution may be withdrawn when valve 21 is open.

Figure 2:
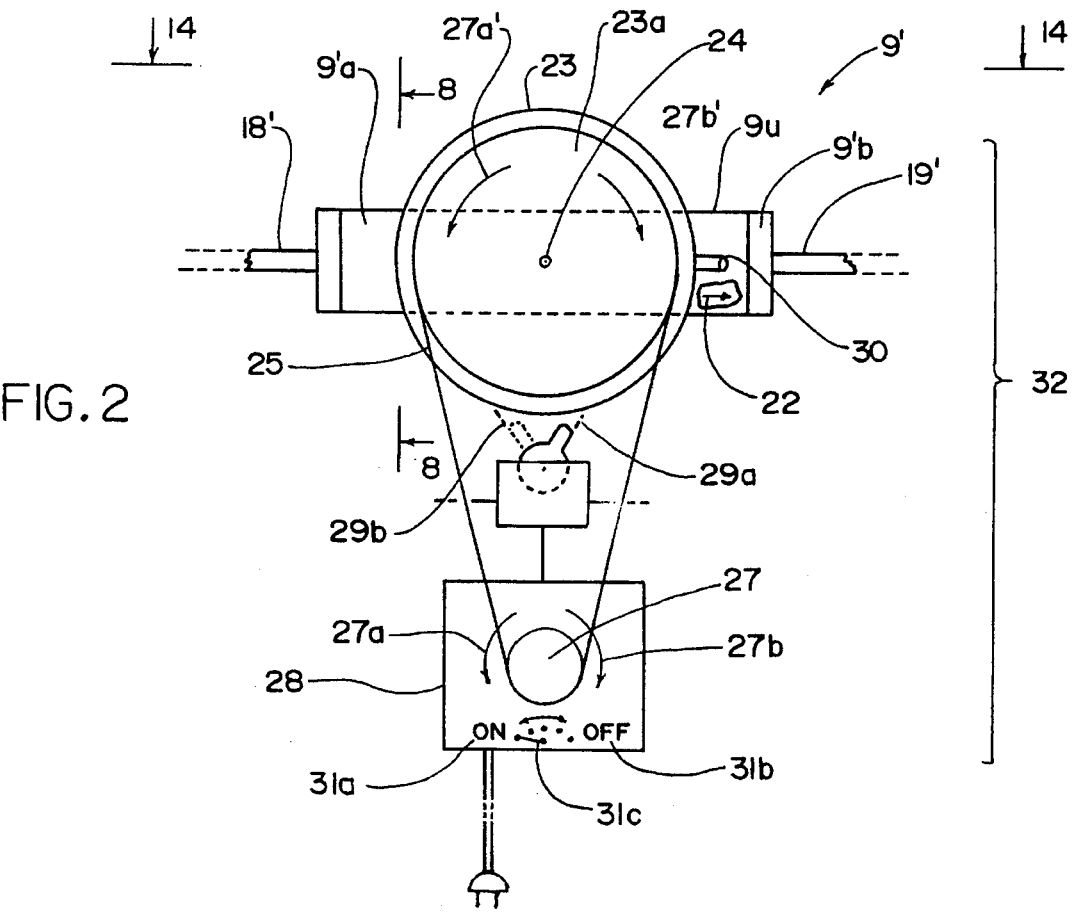
FIG. 2 diagrammatically and symbolically illustrates the reciprocatable flow-cell and a typical preferred mechanism for bringing about the alternate reciprocation of the flow-cell, shown is side view.

FIG. 2 illustrates in greater detail one embodiment 9' of the structures and mechanism thereof of the reciprocatable flow-cell 9', illustrating broadly in side view a cylindrical flow-cell 9u of this invention for causing alternate reciprocation of the reciprocatable flow-cell 9'. FIG. 2 diagrammatically and symbolically illustrates the reciprocatable flow-cell 9', and opposite inlet end 9'a and outlet end 9'b and conduits 18' and 19' (shown in-part) connected thereto, and flowing solvent 21 (seen in cut-away portion of the reciprocatable flow-cell) flowing in direction 22. Also there is shown a typical preferred mechanism for bringing about the alternate reciprocation of the reciprocatable flow-cell. That mechanism include the reciprocatable flow-cell 9a being fixedly mounted on and moveable with an alternately revolvable wheel-structure 23 revolvable around a pivot-point axis 24 (appropriately mounted by suspending structure—not shown), with a belt or chain member 25 wrapped sufficiently tightly or otherwise drivable around each of the driven gear 23a rigidly mounted on and revolvable with the wheel-structure 23. The driving chain or belt 25 is mounted driveably around the driven gear 23a and around the drive wheel 27 of reversible drive motor 28. The drive motor 28 drives the drive wheel in one direction of directions 27a and 27b when the switch key 29 is in one of positions 29a and 29b, and in an opposite direction when the key 30 strikes and move the key 29 to a remaining one of positions 29a and 29b. The belt or chain member 25 is alternately driven as the direction of the of the drive motor is reversed by the switch 29. There additionally is an on-off switch switchable between alternate on-position 31a and off-position 31b, by manually alternately moveable lever 31c. All illustrations of this Figure are shown is side view. The driving mechanism illustrated herein is utilizable with any flow-cell shape comparable with the definitions of the present invention.

Figure 3:
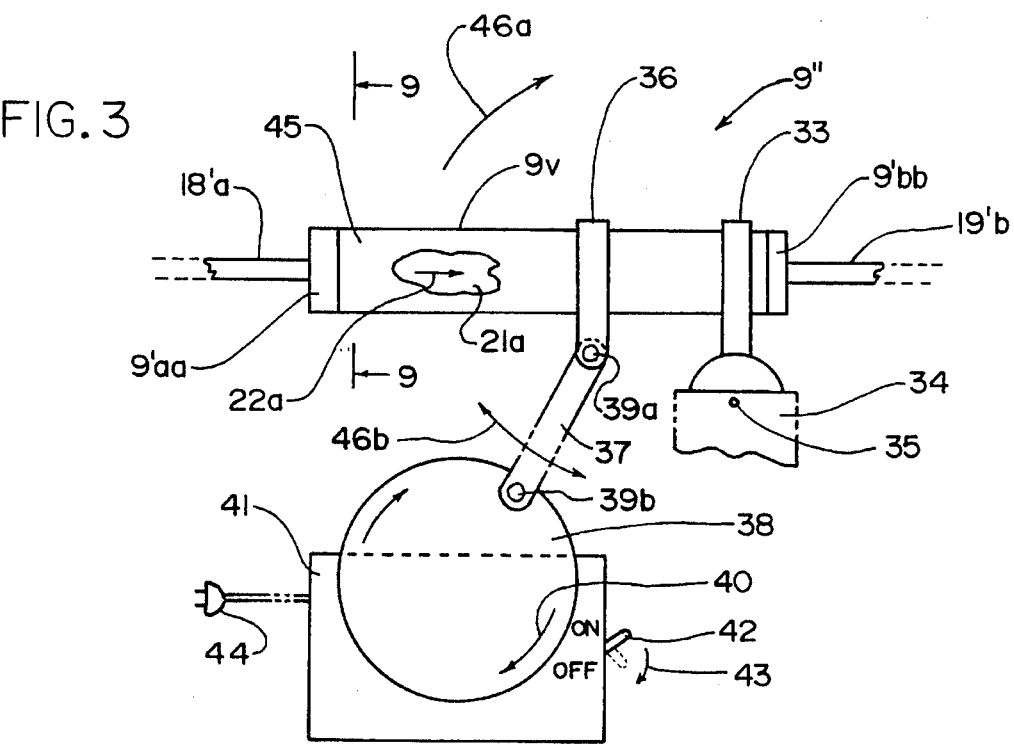
FIG. 3 diagrammatically and symbolically illustrates the reciprocatable flow-cell and an alternate typical preferred mechanism for bringing about the alternate reciprocation of the flow-cell, shown in side view.

FIG. 3 diagrammatically and symbolically illustrates the reciprocatable flow-cell 9v and an alternate typical preferred alternating mechanism jointly identified as 9''' for bringing about the alternate reciprocation of any flow cell within the scope of this invention as herein defined, but this Figure also illustrating again the same-shaped embodiment as the reciprocatable flow-cell of FIG. 1, namely cylindrical (both inside and outside walls), in this particular embodiment, shown in side view. The reciprocatable flow-cell 9'b is rigidly mounted by structure 33 at one end thereof and pivotably mounted at an opposite remaining end thereof onto a pivot structure 34 on a typical pivot pin 35. At a distal position other attaching structure is mounted thereof and connected indirectly by a pivoted lever intermediate arm to a revolving wheel by alternate pins 39a and 39b with the wheel being revolvable in revolving direction (or equally operable in an opposite direction) as driven by motor 41 having an on-off switch 42 with alternate switch-direction 43, with a power source 44. Thereby, when activated to revolve the wheel 38, the reciprocatable flow-cell's distal end 45 moves alternately upwardly and downwardly along the arcs 46a and 46b respectively, while the diluent/solvent flow in direction 22a —the same relative direction as shown in FIG. 2 in flow space 21a. There are shown the previously illustrated corresponding inlet structure 9'aa and outlet structure 9'bb and inlet conduit 18'a and outlet conduit 19'b.

Figure 4:
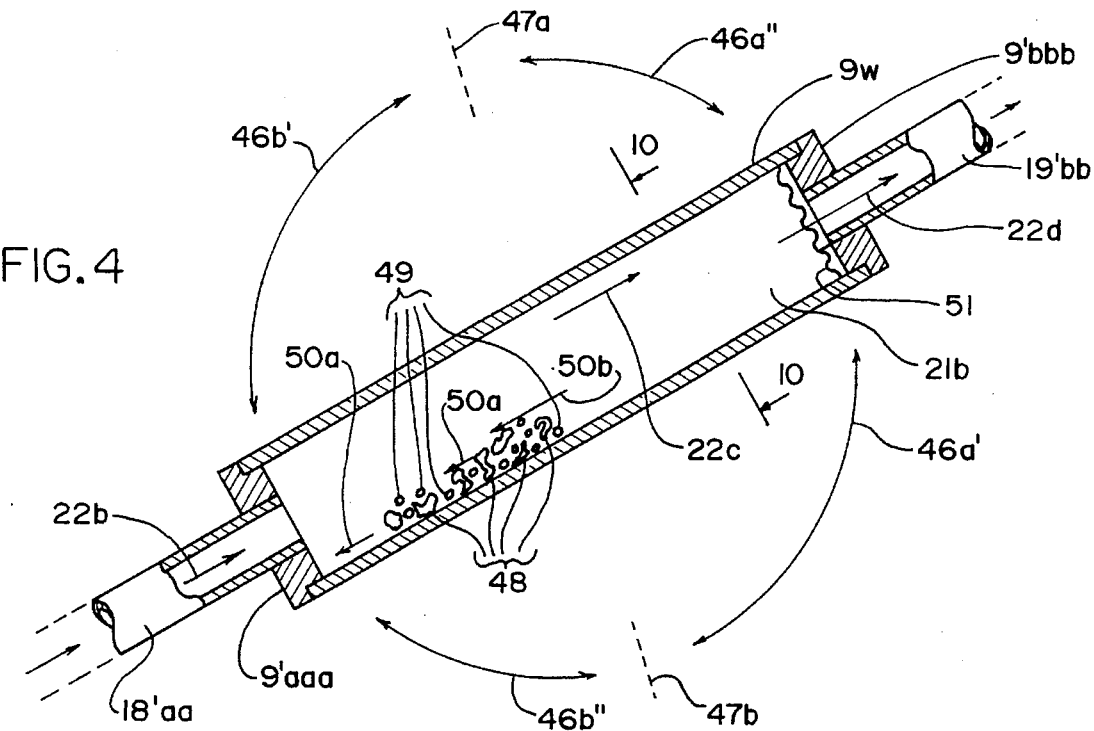
FIG. 4 diagrammatically and symbolically illustrates a cylindrically shaped flow cell in cross-sectional side view, and its directions of alternate reciprocation and the flow-cell itself, with inlet and outlet and in-part views of inlet conduit and outlet conduit mounted at the inlet and the outlet respectively, together with diluent/solvent flow within the flow-space of the flow-cell, together with undissolved solute within the flow space, together with insoluble beads within the flow space, together with illustrating the paths of reciprocatable reciprocation.

FIG. 4 diagrammatically and symbolically illustrates a cylindrically shaped flow cell 9w in cross-sectional side view and may be mounted by any alternate reciprocating mechanism such a typically illustrated in the preferred embodiments of FIGS. 2 and 3, together with its directions of alternate reciprocations of the flow-cell itself with inlet end 9'aaa and outlet end 9'bbb and inlet conduit 18'aa, and flow directions 22b, 22c and 22d in flow space 21b, and outlet conduit 19'bb. There is illustrated undissolved solute 48 within the flow space 21b moveable in direction 50a, together with insoluble beads 49 within the flow space moveable therein in direction 50b when the inlet end 9'aaa as herein illustrated in at a lower level than the outlet end 9'bbb. Also, there is illustrated the paths of reciprocatable reciprocation 46a'–46a" and 46b'–46b" respectively between the alternate vertical positions after up to 180 degrees arcuate movement alternately in each of opposite directions from the perpendicular 47a–47b. Also, as is preferably present in each embodiment, there is shown the mounted screen 51 mounted in close proximity to the outlet end within space 21b, to screen out any undissolved solute and/or flowing or rolling of bead(s) or equivalent insoluble object toward and/or out of the outlet end.

Figure 5:
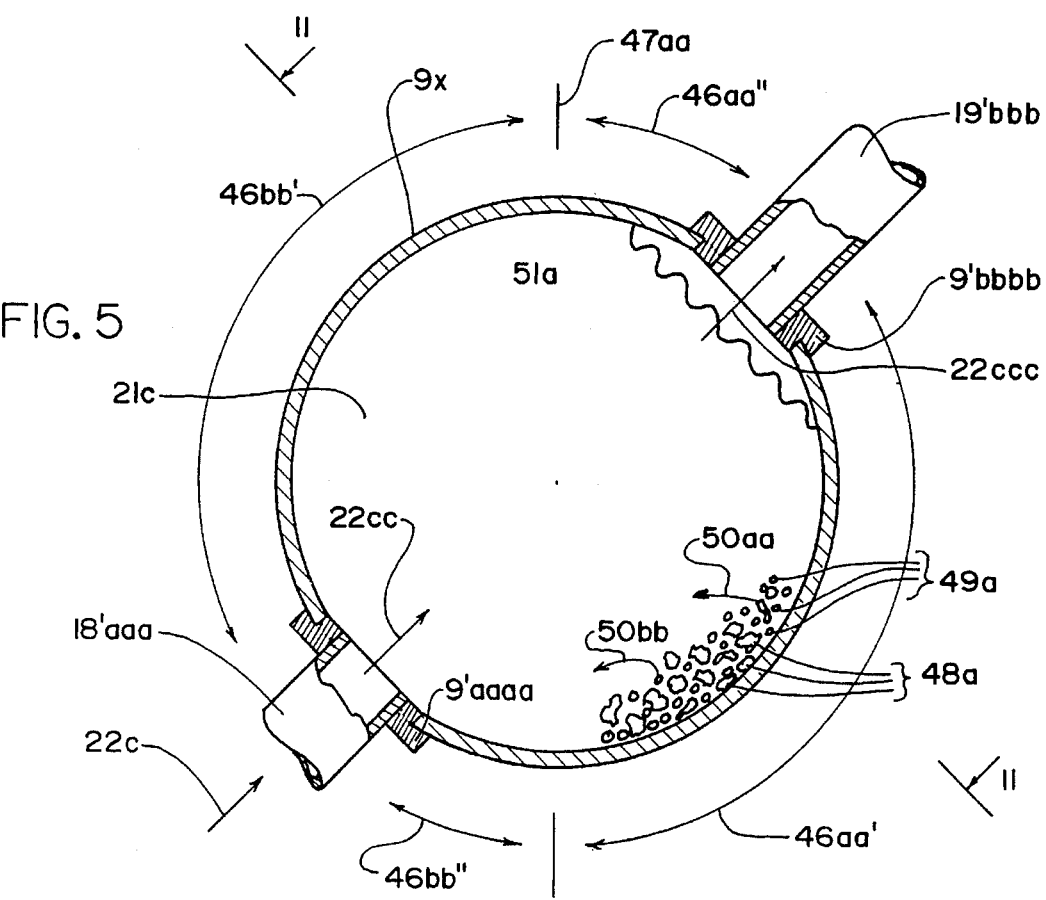
FIG. 5 diagrammatically and symbolically illustrates an alternate spherically shaped (hollow) embodiment of the flow-cell in cross-sectional view, and its directions of alternate reciprocation and the flow-cell itself, with inlet and outlet and in-part views of inlet conduit and outlet conduit mounted at the inlet and the outlet respectively, together with diluent/solvent flow within the flow-space of the flow-cell, together with undissolved solute within the flow space, together with insoluble beads within the flow space, together with illustrating the paths of reciprocation.

FIG. 5 diagrammatically and symbolically illustrates an alternate spherically shaped (hollow) embodiment of the flow-cell 9w in cross-sectional view. There may be an entire global type sphere, inside and outside, or alternately (not illustrated, an equivalent function would be achieved by being around in this view as illustrated—but disk shaped in width in the alternate unillustrated equivalent embodiment. For the FIG. 5 embodiment, also illustrated are its directions 46bb', 46bb", 46aa", 46aa' of alternate reciprocation, with inlet 9'aaaa and outlet 9'bbbb and in-part views of the inlet conduit 18'aaa and outlet conduit 19'bbb mounted at the inlet and the outlet respectively, together with diluent/solvent flow within the flow-space of the flow-cell in directions 22c, 22cc and 22ccc, together with undissolved solute 48a within the flow space 21c moveable in direction 50aa, together with insoluble beads 49a within the flow space moveable in direction 50bb, when the inlet end is lower than the outlet end, as illustrated in this Figure.

Figure 6:
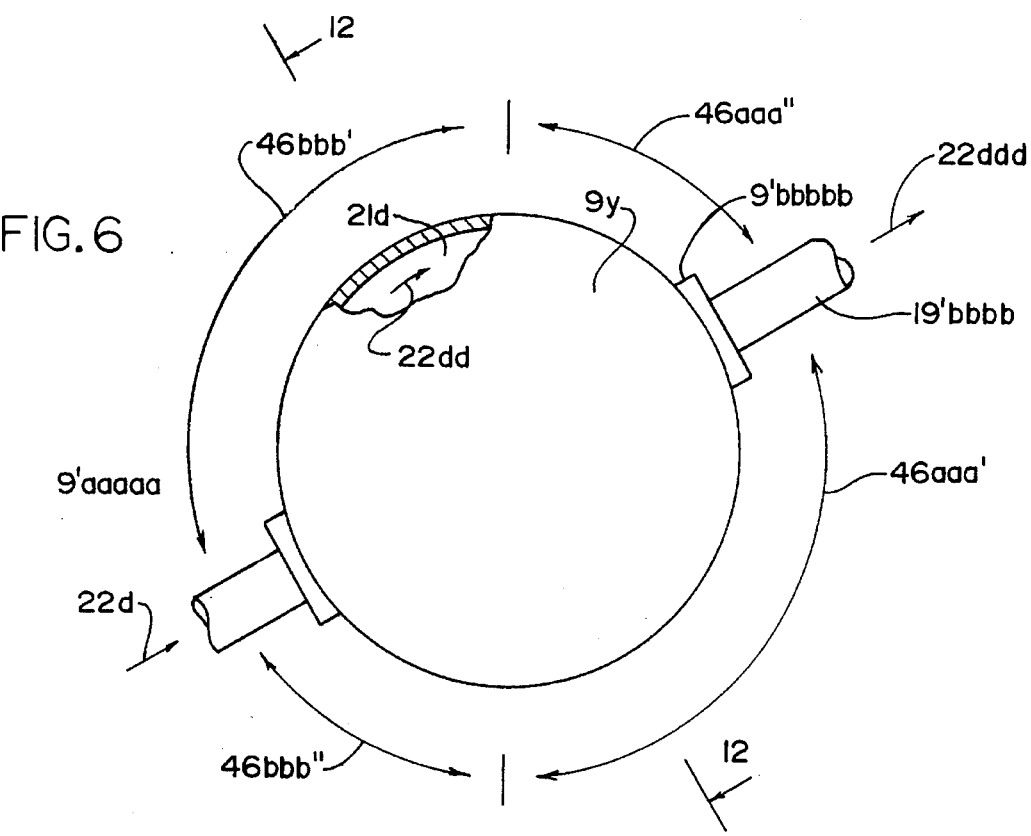
FIG. 6 diagrammatically and symbolically illustrates an alternate elliptically shaped embodiment of the flow-cell in cross-sectional view, and its directions of alternate reciprocation and the flow-cell itself, with inlet and outlet and in-part views of inlet conduit and outlet conduit mounted at the inlet and the outlet respectively, together with diluent/ solvent flow within the flow-space of the flow-cell, together with illustrating the paths of reciprocatable reciprocation.

FIG. 6 diagrammatically and symbolically illustrates an alternate elliptically shaped embodiment (elliptical or substantially circular in cross-sectional direction therethrough—across the path of flow) of the flow-cell 9y in cross-sectional view, and its directions 46aaa", 46aaa', 46bbb', and 46bbb" of alternate reciprocation and the flow-cell itself, with inlet end 9'aaaaa and outlet end 9'bbbbb and in-part views of inlet conduit 18'aaaa and outlet conduit 19'bbbb mounted at the inlet end and the outlet end respectively, together with diluent/solvent flow within the flow-space 21d of the flow-cell in directions 222d, 22dd and 22ddd, together with illustrating the paths of reciprocatable reciprocation. Likewise in this embodiment, as an alternate thereto, the elliptical shape may be solely in the upright direction as shown herein, with the width being such that the structure is disk shaped extending between the inlet end and the outlet end—as an equivalent but not illustrated embodiment.

Figure 7:
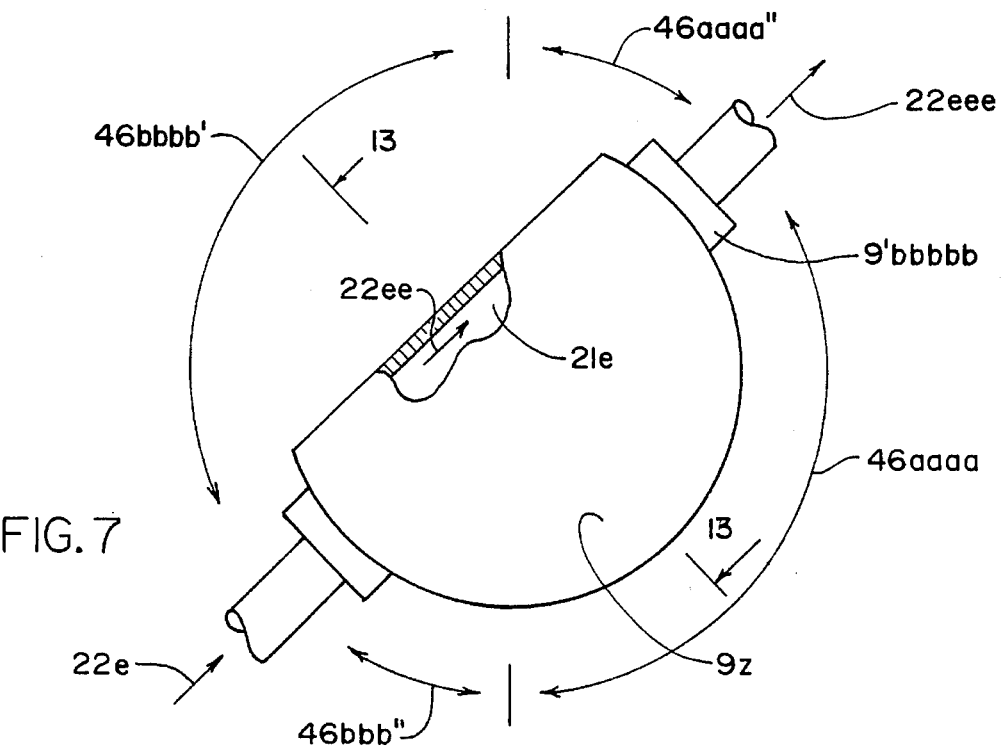
FIG. 7 diagrammatically and symbolically illustrates an alternate hemispherically shaped embodiment of the flow-cell in cross-sectional view, and its directions of alternate reciprocation and the flow-cell itself, with inlet and outlet and in-part views of inlet conduit and outlet conduit mounted at the inlet and the outlet respectively, together with diluent/solvent flow within the flow-space of the flow-cell, together with illustrating the paths of reciprocatable reciprocation.

FIG. 7 diagrammatically and symbolically illustrates an alternate hemispherically shaped embodiment of the flow-cell 9z in cross-sectional view, and its directions of alternate reciprocation and the flow-cell itself, with inlet and outlet and in-part views of inlet conduit and outlet conduit mounted at the inlet and the outlet respectively, together with diluent/solvent flow within the flow-space of the flow-cell, together with illustrating the paths of reciprocatable reciprocation. This embodiment corresponds in substantially all regards and identifications to the embodiment of FIG. 5, except that this embodiment illustrates a hemispherical shape—inside and out as a functional equivalent, rather than the FIG. 5 spherical shape.

FIG. 8 illustrates a cross-sectional view as taken along line 8—8 of FIG. 2.

FIG. 9 illustrates a cross-sectional view as taken along line 9—9 of FIG. 3.

FIG. 10 illustrates a cross-sectional view as taken along line 10—10 of FIG. 4.

FIG. 11 illustrates a cross-sectional view as taken along line 11 of FIG. 5.

FIG. 12 illustrates a cross-sectional view as taken along line 12—12 of FIG. 6.

FIG. 13 illustrates a cross-sectional view as taken along line 13—13 of FIG. 7.

FIG. 14 is a symbolic and diagrammatic representation of the aforenoted invention as illustrated along line 14—14 of FIG. 2. In this view additional structure and mechanism is disclosed for supporting concurrently a plurality of flow-cells $9u$, $9u'$, $9u''$, and $9u'''$—for each and all thereof, for alternately raising and lowering one or both of (1) the inlet ends $9'$, $9'a$, $9'b$, $9'c$ and (2) the outlet ends $9'b$, $9'ba$, $9'ba$, $9'ba$ of the plurality of flow-cells relative one to the another or to each other. The arrangement is such that a single drive and combination represented by specifically illustrated FIG. 2 or alternately on any and all of FIGS. 2 through 7 may function concurrently function for the plurality as driven by a typical common drive motor 28, for either identical and/or different solute(s) and/or suspendable aggregate(s) and/or solvent(s) and/or diluent(s). The illustrated plurality of flow-cells of FIG. 14 are merely here typically mounted between upper downwardly-pressed slat 52a (typically having a lower flat or scalloped face) and a lower upwardly-pressed slat 52b (typically having an upper upwardly-pressed flat or scalloped face), gripped therebetween sturdily and immovably relative to the gripping slats. Typically the upper slat is manually releasable intermittently sufficiently to initially insert and subsequently remove one or more of the supported and anchored flow cells of the plurality. The opposite ends of the slats 52a and 52b are mounted between typically upper ends and between lower ends of the upright spaced-apart support structures 53a and 53b. The upright spaced-apart upright structures are each and both fixedly typically rigidly mounted onto the alternately rotatable aforestated axis 24 mounted on and extending between structures 54a and 54b, alternately driven by the aforestated driving wheel 23 by the aforestated driving belt 27 previously described for FIG. 2.

In light of the foregoing, it will be appreciated that upon at-least initially feeding diluent and/or solvent from the diluent source 15 through diluent source outlet 15a through conduit 16 in direction 16a into variable valve inlet 12b through the variable valve 12 outwardly from the variable valve outlet 12c through the pump-connecting inlet conduit 17 in direction 17 into and through the pump 10 at a rate preset or altered from time to time, by the variable rate-of-flow automatic and/or manually set regulator 11, the diluent is thereby pumped from the pump 10 though pump outlet 18a into the flow-cell's inlet 9a through the flow-cell 9 and thereafter out of the flow-cell's outlet 9b through flow-cell out-conduit 19 in direction 19a through the solution and/or suspension collection vessel's inlet 14a into the solution and/or suspension collection vessel 14. Once there is sufficient solvent and/or diluent in the flow-cell 9, if desired and/or expedient under all surrounding circumstances and the nature of the solute and/or diluent being utilized, pressure/rate of flow, etc., the variable valve 12 may be turned/switched to in whole or in-part circulate solution from the solution collection vessel 14 through the outlet 14b thereof through the cyclic or return-flow conduit 13 in direction 13a into and through the variable valve cyclically thereafter through the aforenoted conduit 15.

The flow rate regulator 11 include a manual regulator mechanism including variable handle 11a having typically a pointer 11b, pivotable around a pivot mounting point 11c from one of several alternate flow rate indicators 11d, allowing for manual adjustment of rate of flow by electrical signal and intensity of current flowing through symbolic regulator lines/wires to the pump 10, when powered by electrical power source 11f, and when the pump 10 is appropriately powered by symbolically a power source 10c. Before and/or during the driving of diluent/solvent through the flow-cell 9, solute and/or suspendable aggregate are introduced into the flow-cell through any convention addition conduit structure and/or through the inlet and/or outlet thereof prior to connection—while not illustrated flow-cells conventionally having solute-addition opening, as is the situation and case for the present invention, not being the heart of the invention. Likewise, before or after adding or pumping-in diluent/solvent into container space of the flow-cell 9, insoluble member(s) such as typically the aforestated insoluble beads 49 may be separately introduced and/or introduced concurrently with soluble solute and/or suspendable aggregate and/or soluble solute.

Immediately upon activation of the pump 10, the reversible drive motor 28 of typically FIG. 2 or the single-direction drive motor 41 typically of FIG. 3 are actuated to assure that alternately the flow-cell 9 becomes alternately tilted as illustrated in foregoing FIGS. 2 or 3, such that intermittently alternatively the solute and/or and/or insoluble aggregate (such as colloidally-suspendable matter) and/or insoluble member (s)) such as insoluble beads) one or more shift and move toward the inlet end $9'a$ by way of gravity, and alternately thereafter when the inlet end is positioned substantially as high as or higher than the outlet end, the solute and/or and/or insoluble aggregate (such as colloidally-suspendable matter) and/or insoluble member (s)) such as insoluble beads) one or more shift and/or move toward the outlet end as a result of one or more of flow rate diluent/solvent pressure and/or gravity toward the aforenoted outlet end.

While some preferred embodiments specifically set-forth preferred rotatable degree-range(s) of movement of one or both around a pivot point, the broad invention as stated do not Limit the number of degrees, since in particular there is an advantage to maximum rotation in a single direction being up to or more than 360 degrees, as follows. In rotating up to a maximum of merely 180 degrees, a heavy (weighty) object (whether soluble or insoluble) would slide or roll solely along what would be a lower inner surface (as identified when in a horizontal position) thereby being effective to push, scrape or nudge sole aggregate (soluble or insoluble) that might be maintaining contact with or sticking-to that inner lower surface, whereas if rotation is up to substantially 360 degrees, during such total revolution also the opposite normally upper inner surface (as well as the lower inner surface) will be alternately inverted and subject to supporting aforenoted slideable or rollable heavy object(s), such that both upper and lower inner surfaces of the vessel are subject to and potentially benefited by the contact of those surfaces with the weighty objects. As a result thereof, greater turbulence is obtained, together with an assurance that there will be enhanced possibility that nothing of a potentially soluble nature is adhered to a surface not contacted or abraded by the weighty object(s). Also, as is conventional in some types of prior art flow-through dissolution conduits discussed above as part of the prior art, it is desirable and important to maintain a "constant" rate of flow of the diluent between the inlet and the outlet, although there may be advantages on occasions for particular differing tests to be performed, that the rate be not always constant, and that the rate vary in some definite degree with regard to the total flow space and/or nature of the particular solute or drug-containing aggregate. Likewise, it is conventional to include as a part of the combination apparatus, a structural mechanism for adjusting pH of the diluent passing between the inlet and the outlet, depending upon the nature of the solute and/or intended eventual use thereof, solubility thereo and/or reactivity thereof, nature of tests to be performed on the extracted solute and/or drug, for example, and the like.

Also, as is conventional in acknowledged prior art flow-through aforenoted arrangements, it is likewise conventional that the apparatus include structure and mechanism for taking sample or predetermined solution (or suspension) volumes of the solute-containing or drug-containing extracted solute, for the testing thereof, while otherwise (if desired) continuing cyclic recirculation of the diluent and/or solution previously exited from the outlet.

It is within the scope of the invention to utilize conventional equipment of the flow-cell type containers, pumps, technology and the likes, in so far as such is consistent with the inventive objects set-forth hereinabove.

It is likewise within the scope of the invention to make such variation(s) and/or modification(s) as would be apparent or obvious to a person of ordinary skill in the art.

We claim:

1. A solute-dissolution reciprocating flow-cell device comprising in combination:
   A) a solute-dissolution flow-cell:
      a) having substantially opposite inlet flow structure and outlet flow structure, having inwardly space-closing walls forming solute-mounting and liquid-flow space therein extending substantially between said inlet flow structure and said outlet flow structure,
      b) said inlet flow structure forming an inlet and said outlet flow structure forming an outlet, said inlet and said outlet each being in flow communication with said liquid flow-space, and
      c) including solute-retaining means for introducing into and retaining undissolved solute within the liquid-flow space substantially between said inlet and said outlet; and
   B) elevation means for alternately raising and lowering at-least one of a) the inlet flow structure and inlet thereof, and b) the outlet flow structure and outlet thereof, at-least one of above and below the other a predetermined number of angular degrees while substantially concurrently obtaining and maintaining at a predetermined rate of movement and flow of solvent between said inlet and said outlet, for jointly (1) said predetermined number of angular degrees to be of sufficient elevation and 2) said predetermined rate to be sufficiently low as to alternately:
      a) permit gravity movement of undissolved solute through liquid flowing in an opposite direction to gravity movement of undissolved solute positioned between said inlet and said outlet within said liquid flow space whenever gravity movement is in a direction toward said inlet and
      b) intermittently alternately permit undissolved solute to move in the same direction as liquid flowing from the inlet to the outlet thereby to alternately shift undissolved solute in opposite directions along said flow path within said liquid flow space, and
   C) pump means for causing liquid to flow from a liquid source sequentially into said inlet, through said flow liquid space and out-of said outlet at said predetermined rate and pressure at-least when said outlet is at an elevation higher than elevation or said inlet.

2. A solute-dissolution reciprocating flow-cell device of claim 1, in which said solute-dissolution flow-cell and flow path thereof are substantially at-least hemispherical in shape.

3. A solute-dissolution reciprocating flow-cell device of claim 2, in which said solute-dissolution flow-cell and flow path thereof are substantially spherical in shape.

4. A solute-dissolution reciprocating flow-cell device of claim 2, in which said solute-dissolution flow-cell and flow path thereof are substantially elliptical in shape.

5. A solute-dissolution reciprocating flow-cell device of claim 2, in which said solute-dissolution flow-cell and flow path thereof are substantially spherical shape.

6. A solute-dissolution reciprocating flow-cell device of claim 1, in which said solute-dissolution flow-cell and flow path thereof are substantially cylindrical and linear between said inlet flow structure and said outlet from structure, and said solute-dissolution flow-cell and flow path thereof are elongated along a longitudinal axis extending substantially between said inlet and said outlet as compared to transverse directions.

7. A solute-dissolution reciprocating flow-cell device of claim 6, in which said solute-dissolution flow-cell has a flow-path cross-section extending substantially from said inlet to said outlet, and including within said flow space at least one substantially insoluble member having an insoluble member cross-section sufficiently smaller than at-least a part of said flow-path cross-section and having amass sufficiently massive as to be moveable by gravity toward said inlet against flow of said solvent at said predetermined pressure when said outlet is at an elevation higher than said inlet.

8. A solute-dissolution reciprocating flow-cell device of claim 7, in which said substantially insoluble member is present in plurality and said plurality being substantially bead-like in shape.

9. A solute-dissolution reciprocating flow-cell device of claim 8, including a heater-circulator means for ascertaining that solvent at a time of entry of solvent through said inlet is substantially maintained substantially at a predetermined desired temperature that is consistent with an ultimate predetermined end us of a predetermined solute or drug to be dissolved within said flow path is at substantially maximum solubility within a predetermined solvent to be circulated into contact with the predetermined solute.

10. A solute-dissolution reciprocating flow-cell device of claim 9, including at-least one heater-circulator ascertainable of and maintainable of substantially optimum solubility temperature of solute-containing solvent that has flowed through said outlet.

11. A solute-dissolution reciprocating flow-cell device of claim 10, including closed-flow means for diverting at-least a portion of solute-containing solvent passing from said outlet, in at-least partially closed flow back to said inlet.

12. A solute-dissolution reciprocating flow-cell device of claim 11, including in parallel on said elevation means a plurality of said solute-dissolution flow-cell mounted for concurrently the elevation means alternately raising thereof at-least one of a) the inlet flow structure and inlet thereof, and b) the outlet flow structure and outlet thereof, of the plurality, such that concurrently at least one of the inlet and the outlet of each of said plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents.

13. A solute-dissolution reciprocating flow-cell device of claim 12, in which substantially average cross-sectional diameter of said flow-space ranges between about 10 mm to about 25 mm and in which said predetermined rate of flow per minute ranges from about 3 milliliters to about 20 milliliters per minute.

14. A solute-dissolution reciprocating flow-cell device of claim 13, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 10 angular degrees and about 180 angular degrees.

15. A solute-dissolution reciprocating flow-cell device of claim 13, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 45 annular degrees and about 90 angular degrees.

16. A solute-dissolution reciprocating flow-cell device of claim 15, in which said elevation means is adapted to pivot concurrently said inlet flow structure downwardly and said outlet flow structure upwardly around a pivot point substantially centrally intermediate between the inlet and the outlet.

17. A solute-dissolution reciprocating flow-cell device of claim 16, in which said undissolved solute is in a liquid state.

18. A solute-dissolution reciprocating flow-cell device of claim 16, including undissolved solute within said liquid flow space substantially between said inlet and said outlet.

19. A solute-dissolution reciprocating flow-cell device of claim 18, including said solvent within said liquid flow space substantially between said inlet and said outlet.

20. A solute-dissolution reciprocating flow-cell device of claim 16, including said solvent within said liquid flow space substantially between said inlet and said outlet.

21. A solute-dissolution reciprocating flow-cell device of claim 20, in which said solvent is predominantly water.

22. A solute-dissolution reciprocating flow-cell device of claim 1, in which said solute-dissolution flow-cell has a flow-path cross-section extending substantially from said inlet to said outlet, and including within said flow space at least one substantially insoluble member having an insoluble member cross-section sufficiently smaller than at-least a part of said flow-path cross-section and having a mass sufficiently massive as to be moveable by gravity toward said inlet against flow of said solvent at said predetermined pressure when said outlet is at an elevation higher than said inlet.

23. A solute-dissolution reciprocating flow-cell device of claim 22, in which said substantially insoluble member is present in plurality and said plurality being substantially bead-like in shape.

24. A solute-dissolution reciprocating flow-cell device of claim 1, including a heater-circulator means for ascertaining that solvent at a time of entry of solvent through said inlet is substantially maintained substantially at a predetermined desired temperature that is consistent with an ultimate predetermined end us of a predetermined solute or drug to be dissolved within said flow path is at substantially maximum solubility within a predetermined solvent to be circulated into contact with the predetermined solute.

25. A solute-dissolution reciprocating flow-cell device of claim 1, including at-least one heater-circulator ascertainable of and maintainable of substantially optimum solubility temperature of solute-containing solvent that has flowed through said outlet.

26. A solute-dissolution reciprocating flow-cell device of claim 1, including closed-flow means for diverting at-least a portion of solute-containing solvent passing from said outlet, in at-least partially closed flow back to said inlet.

27. A solute-dissolution reciprocating flow-cell device of claim 1, including in parallel on said elevation means a plurality of said solute-dissolution flow-cell mounted for concurrently the elevation means alternately raising thereof at-least one of a) the inlet flow structure and inlet thereof, and b) the outlet flow structure and outlet thereof, of the plurality, such that concurrently at least one of the inlet and the outlet of each of said plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents.

28. A solute-dissolution reciprocating flow-cell device of claim 1, in which substantially average cross-sectional diameter of said flow-space ranges between about 10 mm to about 25 mm and in which said predetermined rate of flow per minute ranges from about 3 milliliters to about 20 milliliters per minute.

29. A solute-dissolution reciprocating flow-cell device of claim 1, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from abut 10 angular degrees and abut 180 angular degrees.

30. A solute-dissolution reciprocating flow-cell device of claim 1, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 45 annular degrees and abut 90 angular degrees.

31. A solute-dissolution reciprocating flow-cell device of claim 1, in which said elevation means is adapted to pivot concurrently said inlet flow structure downwardly and said outlet flow structure upwardly around a pivot point substantially centrally intermediate between the inlet and the outlet.

32. A solute-dissolution reciprocating flow-cell device of claim 1, in which said undissolved solute is in a liquid state.

33. A solute-dissolution reciprocating flow-cell device of claim 1, including undissolved solute within said liquid flow space substantially between said inlet and said outlet.

34. A solute-dissolution reciprocating flow-cell device of claim 33, including said solvent within said liquid flow space substantially between said inlet and said outlet.

35. A solute-dissolution reciprocating flow-cell device of claim 1, including said solvent within said liquid flow space substantially between said inlet and said outlet.

36. A solute-dissolution reciprocating flow-cell device of claim 35, in which said solvent is predominantly water.

37. A solute-dissolution reciprocating flow-cell device comprising in combination:

A) a solute-dissolution flow-cell:
  a) having substantially opposite inlet-flow structure and outlet flow structure, having inwardly space-closing walls forming solute-mounting and liquid-flow space therein extending substantially between said inlet flow structure and said outlet flow structure,
  b) said inlet flow structure forming an inlet and said outlet flow structure forming an outlet, said inlet and said outlet each being in flow communication with said liquid flow-space,
  c) including solute-retaining means for introducing into and retaining undissolved solute within the liquid-flow space substantially between said inlet and said outlet;
  d) said solute-dissolution flow-cell having a flow-path cross-section extending substantially from said inlet to said outlet; and
  e) there being within said flow space at least one substantially insoluble member having an insoluble member cross-section sufficiently smaller than at-least a part of said flow-path cross-section as to be moveable along said flow path; and B) elevation means for alternately raising and lowering at-least one of a) the inlet flow structure and inlet thereof, and b) the outlet flow structure and outlet thereof, at-least one of above and below the other a predetermined number of angular degrees while substantially concurrently obtaining and maintaining at a predetermined rate of movement and flow of solvent between said inlet and said outlet, for jointly (1) said predetermined number of angular degrees to be of sufficient elevation and 2) said predetermined rate to be sufficiently low as to alternately:
  a) permit gravity movement of said at least one substantially insoluble member through liquid flowing in an opposite direction to gravity movement of said at least one substantially insoluble member positioned between said inlet and said outlet within said liquid flow space whenever gravity movement is in a direction toward said inlet and
  b) intermittently alternately permit the at least one insoluble member to move in the same direction as liquid flowing from the inlet to the outlet thereby to alternately shift the at least one insoluble member to move alternately in opposite directions along said flow path within said liquid flow space, and C) pump means for causing liquid to flow from a liquid source sequentially into said inlet, through said flow liquid space and out-of said outlet at said predetermined rate and pressure at-least when said outlet is at an elevation higher than elevation of said inlet.

38. A solute-dissolution reciprocating flow-cell device of claim 37, in which said solute-dissolution flow-cell and flow path thereof are substantially at-least hemispherical in shape.

39. A solute-dissolution reciprocating flow-cell device of claim 38, in which said solute-dissolution flow-cell and flow path thereof are substantially spherical in shape.

40. A solute-dissolution reciprocating flow-cell device of claim 38, in which said solute-dissolution flow-cell and flow path thereof are substantially elliptical in shape.

41. A solute-dissolution reciprocating flow-cell device of claim 38, in which said solute-dissolution flow-cell and flow path thereof are substantially spherical in shape.

42. A solute-dissolution reciprocating flow-cell device of claim 37, in which said solute-dissolution flow-cell and flow path thereof are substantially cylindrical and linear between said inlet flow structure and said outlet flow structure, and said solute-dissolution flow-cell and flow path thereof are elongated along a longitudinal axis extending substantially between said inlet and said outlet as compared to transverse directions.

43. A solute-dissolution reciprocating flow-cell device of claim 37, in which said substantially insoluble meatier is present in plurality and said plurality being substantially bead-like in shape.

44. A solute-dissolution reciprocating flow-cell device of claim 43, including a heater-circulator means for ascertaining that solvent at a time of entry of solvent through said inlet is substantially maintained substantially at a predetermined desired temperature that is consistent with an ultimate predetermined end us of a predetermined solute or drug to be dissolved within said flow path is at substantially maximum solubility within a predetermined solvent to be circulated into contract with the predetermined solute.

45. A solute-dissolution reciprocating flow-cell device of claim 44, including at-least one heater-circulator ascertainable of and maintainable of substantially optimum solubility temperature of solute-containing solvent that has flowed through said outlet.

46. A solute-dissolution reciprocating flow-cell device of claim 45, including closed-flow means for diverting at-least a portion of solute-containing solvent passing from said outlet, in at-least partially closed flow back to said inlet.

47. A solute-dissolution reciprocating flow-cell device of claim 46, including in parallel on said elevation means a plurality of said solute-dissolution flow-cell mounted for concurrently the elevation means alternately raising thereof at-least one of a) the inlet flow structure and inlet thereof, and b) the outlet flow structure and outlet thereof, of the plurality, such that concurrently at least one of the inlet and the outlet of each of said plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents.

48. A solute-dissolution reciprocating flow-cell device of claim 47, in which substantially average cross-sectional diameter of said flow-space ranges between about 10 mm to about 25 mm and in which said predetermined rate of flow per minute ranges from about 3 milliliters to about 20 milliliters per minute.

49. A solute-dissolution reciprocating flow-cell device of claim 48, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 10 angular degrees and about 180 angular degrees.

50. A solute-dissolution reciprocating flow-cell device of claim 48, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 45 angular degrees and about 90 angular degrees.

51. A solute-dissolution reciprocating flow-cell device of claim 50, in which said elevation means is adapted to pivot concurrently said inlet flow structure downwardly and said outlet flow structure upwardly around a pivot point substantially centrally intermediate between the inlet and the outlet.

52. A solute-dissolution reciprocating flow-cell device of claim 51, including undissolved solute within said liquid flow space substantially between said inlet and said outlet.

53. A solute-dissolution reciprocating flow-cell device of claim 52, including said solvent within said liquid flow space substantially between said inlet and said outlet.

54. A solute-dissolution reciprocating flow-cell device of claim 51, including said solvent within said liquid flow space substantially between said inlet and said outlet.

55. A solute-dissolution reciprocating flow-cell device of claim 54, in which said solvent is predominantly water.

56. A solute-dissolution reciprocating flow-cell device of claim 37, in which said solute-dissolution flow-cell has a flow-path cross-section extending substantially from said inlet to said outlet, and including within said flow space at least one substantially insoluble member having an insoluble member cross-section sufficiently smaller than at-least a part of said flow-path cross-section and having a mass sufficiently massive as to be moveable by gravity toward said inlet against flow of said solvent at said predetermined pressure when said outlet is at an elevation higher than said inlet.

57. A solute-dissolution reciprocating flow-cell device of claim 56, in which said substantially insoluble member is present in plurality and said plurality being substantially bead-like in shape.

58. A solute-dissolution reciprocating flow-cell device of claim 57, predetermined number of angular degrees while substantially concurrently obtaining and maintaining at predetermined rate of movement and flow of solvent between said inlet and said outlet, for jointly (1) said predetermined number of angular degrees to be of sufficient elevation and 2) said predetermined rate to be sufficiently low as to alternately:
   a) permit gravity movement of undissolved solute through liquid flowing in an opposite direction to gravity movement of undissolved solute positioned between said inlet and said outlet within said liquid flow space whenever gravity movement is in a direction toward said inlet and
   b) intermittently alternately permit undissolved solute to move in the same direction as liquid flowing from the inlet to the outlet thereby to alternately shift undissolved solute in opposite directions along said flow path within said liquid flow space.

59. A solute-dissolution reciprocating flow-cell device of claim 58, in which said undissolved solute is in a liquid state.

60. A solute-dissolution reciprocating flow-cell device of claim 37, including a heater-circulator means for ascertaining that solvent at a time of entry of solvent through said inlet is substantially maintained substantially at a predetermined desired temperature that is consistent with an ultimate predetermined end us of a predetermined solute or drug to be dissolved within said flow path is at substantially maximum solubility within a predetermined solvent to be circulated into contact with the predetermined solute.

61. A solute-dissolution reciprocating flow-cell device of claim 37, including at-least one heater-circulator ascertainable of and maintainable of substantially optimum solubility temperature of solute-containing solvent that has flowed through said outlet.

62. A solute-dissolution reciprocating flow-cell device of claim 37, including closed-flow means for diverting at-least a portion of solute-containing solvent passing from said outlet, in at-least partially closed flow back to said inlet.

63. A solute-dissolution reciprocating flow-cell device of claim 37, including in parallel on said elevation means a plurality of said solute-dissolution flow-cell mounted for concurrently the elevation means alternately raising thereof at-least one of a) the inlet flow structure and inlet thereof, and b) the outlet flow structure and outlet thereof, of the plurality, such that concurrently at least one of the inlet and the outlet of each of said plurality are concurrently moved at-least one of above and below the other while substantially concurrently obtaining and maintaining at predetermined rate of movement and flow of solvent between respective inlets and outlet thereof, whereby a plurality of different solutes may be concurrently dissolved in different solvents.

64. A solute-dissolution reciprocating flow-cell device of claim 37, in which substantially average cross-sectional diameter of said flow-space ranges between about 10 mm to about 25 mm and in which said predetermined rate of flow per minute ranges from about 3 milliliters to about 20 milliliters per minute.

65. A solute-dissolution reciprocating flow-cell device of claim 37, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 10 angular degrees and about 180 angular degrees.

66. A solute-dissolution reciprocating flow-cell device of claim 37, in which said elevation means is adapted to move at-least one of said inlet flow structure and said outlet flow structure relative to at-least one of a) a pivot point therebetween and b) a remaining other of said inlet flow structure and said outlet flow structure, through an angle of said predetermined angular degrees ranging from about 45 angular degrees and about 90 angular degrees.

67. A solute-dissolution reciprocating flow-cell device of claim 37, in which said elevation means is adapted to pivot concurrently said inlet flow structure downwardly and said outlet flow structure upwardly around a pivot point substantially centrally intermediate between the inlet and the outlet.

68. A solute-dissolution reciprocating flow-cell device of claim 37, predetermined number of angular degrees while substantially concurrently obtaining and maintaining at predetermined rate of movement and flow of solvent between said inlet and said outlet, for jointly (1) said predetermined number of angular degrees to be of sufficient elevation and 2) said predetermined rate to be sufficiently low as to alternately:
   a) permit gravity movement of undissolved solute through liquid flowing in an opposite direction to gravity movement of undissolved solute positioned between said inlet and said outlet within said liquid flow space whenever gravity movement is in a direction toward said inlet and
   b) intermittently alternately permit undissolved solute to move in the same direction as liquid flowing from the inlet to the outlet thereby to alternately shift undissolved solute in opposite directions along said flow path within said liquid flow space.

69. A solute-dissolution reciprocating flow-cell device of claim 37, in which said undissolved solute is in a liquid state.

70. A solute-dissolution reciprocating flow-cell device of claim 37, in which said predetermined rate of movement and flow of solvent between said inlet and said outlet is sufficiently low as to alternately:
   a) permit gravity movement of dissolved solute through liquid flowing in an opposite direction to gravity movement of undissolved solute positioned between said inlet and said outlet within said liquid flow space whenever gravity movement is in a direction toward said inlet and b) intermittently alternately permit undissolved solute to move in the same direction as liquid flowing from the inlet to the outlet thereby to alternately shift undissolved solute in opposite directions along said flow path within said liquid flow space.

71. A solute-dissolution reciprocating flow-cell device of claim 37, including undissolved solute within said liquid flow space substantially between said inlet and said outlet.

72. A solute-dissolution reciprocating flow-cell device of claim 71, including said solvent within said liquid flow space substantially between said inlet and said outlet.

73. A solute-dissolution reciprocating flow-cell device of claim 37, including said solvent within said liquid flow space substantially between said inlet and said outlet.

74. A solute-dissolution reciprocating flow-cell device of claim 73, in which said solvent is predominantly water.

* * * * *